United States Patent [19]

Irwin

[11] 4,245,082
[45] Jan. 13, 1981

[54] POLYESTERS DERIVED FROM 3,4'-DIHYDROXY-BENZOPHENONES OR 3-HYDROXY-4'-(4-HYDROXYPHENYL-)BENZOPHENONE AND CERTAIN AROMATIC DICARBOXYLIC ACIDS AND FILAMENTS THEREOF

[75] Inventor: Robert S. Irwin, Wilmington, Del.

[73] Assignee: E. I. Du Pont de Nemours and Company, Wilmington, Del.

[21] Appl. No.: 54,448

[22] Filed: Jul. 9, 1979

Related U.S. Application Data

[63] Continuation-in-part of Ser. No. 931,906, Aug. 8, 1978, abandoned.

[51] Int. Cl.$^3$ .................... C08G 63/12; C08G 63/18
[52] U.S. Cl. .................... 528/128; 528/125; 528/220
[58] Field of Search .................... 528/125, 128, 220

[56] References Cited

U.S. PATENT DOCUMENTS

| | | | |
|---|---|---|---|
| 2,464,270 | 3/1949 | Bender et al. | 528/128 |
| 3,028,364 | 4/1962 | Conix et al. | 528/128 |
| 3,531,435 | 9/1970 | Wear | 528/125 |
| 4,075,172 | 2/1978 | Ozawa et al. | 528/183 |
| 4,083,829 | 4/1978 | Calundann et al. | 528/194 |

FOREIGN PATENT DOCUMENTS

| | | | |
|---|---|---|---|
| 2053274 | 4/1971 | France | 528/128 |
| 883312 | 11/1961 | United Kingdom | 528/128 |
| 891781 | 3/1962 | United Kingdom | 528/125 |
| 897640 | 5/1962 | United Kingdom | 528/128 |
| 907647 | 10/1962 | United Kingdom | 528/128 |
| 984524 | 2/1965 | United Kingdom | 528/190 |

*Primary Examiner*—Lester L. Lee

[57] ABSTRACT

High modulus filaments are melt-spun from polyesters which are derived from 3,4'-dihydroxybenzophenones or 3-hydroxy-4'-(4-hydroxyphenyl-)benzophenone and terephthalic, 2,6-naphthalene dicarboxylic, or bibenzoic acid. The polyesters are optically anisotropic in the melt. As-spun filaments from these polyesters can be heat treated while free from tension to increase their tenacity.

15 Claims, No Drawings

POLYESTERS DERIVED FROM 3,4'-DIHYDROXY-BENZOPHENONES OR 3-HYDROXY-4'-(4-HYDROXYPHENYL-)BENZOPHENONE AND CERTAIN AROMATIC DICARBOXYLIC ACIDS AND FILAMENTS THEREOF

CROSS REFERENCE TO RELATED APPLICATION

This application is a continuation-in-part of my copending and coassigned patent application Ser. No. 931,906 filed Aug. 8, 1978 and now abandoned.

BACKGROUND OF THE INVENTION

1. Field of the Invention

This invention pertains to fiber-forming melt-spinnable aromatic polyesters and to high modulus filaments thereof.

2. Description of the Prior Art

A class of aromatic polyesters that form optically anisotropic melts from which oriented filaments can be melt-spun has been described in U.S. Pat. No. 4,118,372 to Schaefgen et al. Other aromatic polyesters that have this property are disclosed in U.S. Pat. No. 4,066,620. The polyesters which are described in the aforementioned references are derived primarily from para-oriented dihydric phenols and para-oriented aromatic dicarboxylic acids. Filaments that are melt-spun from such polyesters can be heat treated to high tenacity and modulus.

This invention provides different aniso-tropic-melt-forming polyesters which can be melt-spun into filaments of high as-spun modulus [e.g., greater than 200 g/denier (177 dN/tex)]. The novel filaments can also be heat treated to increase their tenacities, preferably to a level in excess of 10 g/denier (8.84 dN/tex), while retaining moduli in excess of 200 g/denier (177 dN/tex).

SUMMARY OF THE INVENTION

The present invention is directed to fiber-forming (co)polyesters that exhibit optical anisotropy in the melt and consist essentially of units having the structural formulas

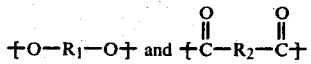

in substantially equimolar amounts and wherein $R_1$ in at least 85 mol % of the

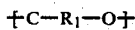

units is

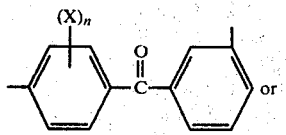

or

in which X is methyl or chloro and n is 0, 1 or 2 and $R_2$ in at least 85 mol % of the

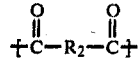

units is selected from the group consisting of p-phenylene, 2,6-naphthylene and p,p'-biphenylene and with the proviso that when n is 1 or 2, $R_2$ in at least 85 mol % of the

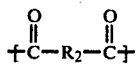

units is selected from 2,6-naphthylene and p,p'-biphenylene. $R_1$ in up to 15 mol % of the

units is selected from the group consisting of m-phenylene, p-phenylene, chloro-p-phenylene, methyl-p-phenylene, p,p'-biphenylene, tetramethyl-p,p'-biphenylene, 2,6-naphthylene and 2,7-naphthylene; and $R_2$ in up to 15 mol % of the

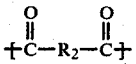

units is m-phenylene. Alternatively the (co)polyesters of the invention consist essentially of units

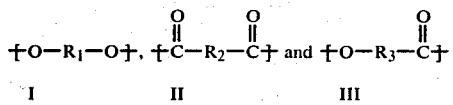

wherein $R_1$ is

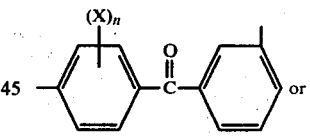

or

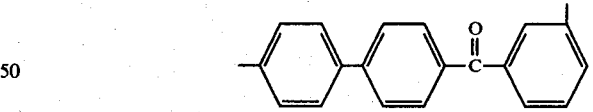

in which X is methyl or chloro and n is 0, 1 or 2, $R_2$ is p-phenylene, 2,6-naphthylene or p,p'-biphenylene and $R_3$ is m- or p-phenylene with unit III constituting up to 15 mol % of the total of units I and III. It also relates to high modulus filaments of such polyesters.

DETAILED DESCRIPTION OF THE INVENTION

The (co)polyesters of the present invention consist essentially of —O—$R_1$—O— units derived from dihydric phenols and

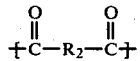

units derived from aromatic dicarboxylic acids in substantially equimolar amounts. At least 85 mol % and preferably all of the —O—R₁—O— units are

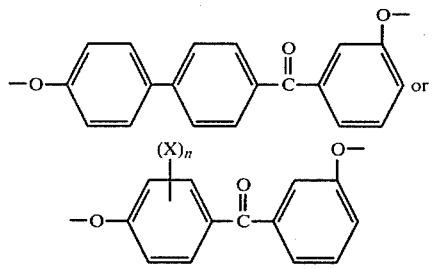

in which X is chloro- or methyl and n is 0, 1 or 2. Preferably n is 0, that is, the unit is unsubstituted. The remaining —O—R₁—O— units, i.e., up to 15 mol %, are selected from the group consisting of

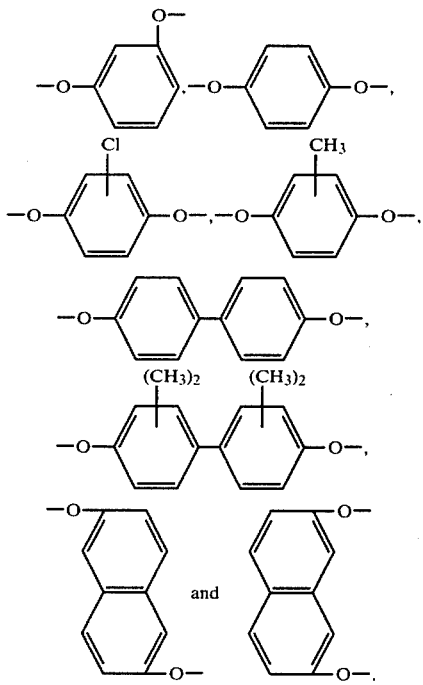

At least 85 mol % and preferably all of the

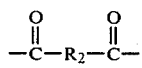

units are selected from the group consisting

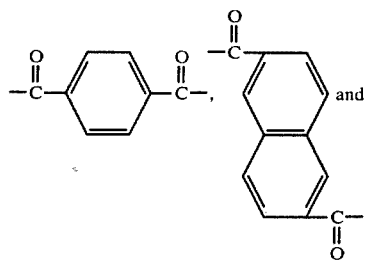

-continued

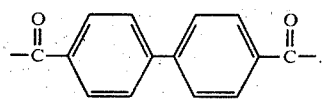

The remaining

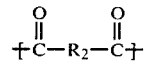

units, i.e., up to 15 mol %, are

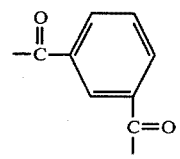

When n is 1 or 2, R₂ must be 2,6-naphthylene or p,p'-biphenylene in at least 85 mol % of the

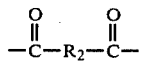

units. Alternatively the (co)polyesters consist essentially of

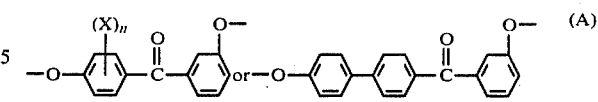

in which X is methyl or chloro and n is 0, 1 or 2, (B) terephthaloyl, 2,6-naphthoyl or p,p'-bi-benzoyl and (C) m- or p-oxybenzoyl units in proportions as defined above.

The (co)polyesters of the invention are capable of forming optically anisotropic melts and have a molecular weight sufficient for melt-spinning into filaments. The term "(co)polyesters" is intended to include both homopolyesters and copolyesters.

Polymerization Conditions

The (co)polyesters may be prepared by standard melt polymerization techniques from one or more aromatic dicarboxylic acids of the formula

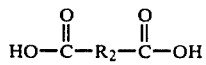

where R₂ is defined as above, and one or more diphenols of the formula HO—R₁—OH where R₁ is defined as above. Frequently the diphenols are employed in their diester form (e.g., diacetate). The diphenols and diacids are normally combined in substantially equimolar amounts and heated in a reaction vessel under nitrogen with stirring for about 1 to 3 hours. Temperatures employed for the polymerization are above the melting points of the reactants and are generally in the range of 200° to 350° C. The reaction vessel is equipped with means to permit by-product removal while polymerization takes place. A vacuum is normally applied towards the end of the polymerization to facilitate removal of remaining by-products and to complete the polymerization. Polymerization conditions such as temperature, duration of heating, pressures, etc., may be varied according to, e.g., the reactants employed and the degree of polymerization desired.

FILAMENT PREPARATION

The (co)polyesters may be spun into filaments by conventional melt-spinning techniques. A melt of the polymer is extruded through a spinneret into a quenching atmosphere (e.g., air or nitrogen maintained at room temperature) and wound up. General spinning conditions are given in U.S. Pat. No. 4,066,620.

As used herein, the term "as-spun" fiber refers to a fiber which has not been drawn or heat treated after extrusion and normal windup.

HEAT TREATMENT AND UTILITY

The as-spun fibers of this invention may be subjected to heat treatment in an oven while relaxed to provide high strength fibers useful for a variety of industrial applications such as plastic and rubber reinforcement. In the heat treating process, fiber samples, as skeins or on bobbins (preferably collapsible bobbins) are usually heated in an inert atmosphere that is continuously purged by flow of inert gas through the oven to remove by-products from the vicinity of the fiber. Temperatures approaching the fusion point but sufficiently below to prevent interfilament fusion are employed. Preferably the maximum temperature is reached in a stepwise fashion.

MEASUREMENTS AND TESTS

Inherent viscosity ($\eta_{inh}$) is defined by the following equation:

$$\eta_{inh} = \frac{\ln(\eta_{rel})}{C}$$

wherein ($\eta_{rel}$) represents the relative viscosity and C represents a concentration of 0.5 gram of the polymer in 100 ml of solvent. The relative viscosity ($\eta_{rel}$) is determined by dividing the flow time in a capillary viscometer of the dilute solution by the flow time for the pure solvent. Flow times are determined at 30° C., and the solvent is p-chlorophenol unless otherwise indicated.

Fiber tensile properties are reported in customary units first with SI units in parentheses.
Denier (D) in g/9000 m. (dtex)
Tenacity (T) in g/denier (dN/tex)
Elongation (E) in percent of unstretched length
Modulus (Mi) in g/denier (dN/tex)
They are measured using the procedures shown in Morgan U.S. Pat. No. 3,827,998 on fibers that have been conditioned for at least one hour. At least three breaks are averaged.

Thermooptical Test (TOT) is described in U.S. Pat. No. 4,066,620. Polymers that pass this test are considered to be optically anisotropic.

The following examples are illustrative of the present invention.

EXAMPLE I—Synthesis of 3,4'-diacetoxybenzophenone

The 3,4'-diacetoxybenzophenone used in subsequent polymerizations was prepared in stages starting from m-anisic acid. It was converted first to m-anisoyl chloride, then to 3,4'-dimethoxybenzophenone, then to 3,4'-dihydroxybenzophenone, and finally to 3,4'-diacetoxybenzophenone. This example provides the details of one such conversion and, except for changes in scale, was the general procedure for all such preparations.

PREPARATION OF M-ANISOYL CHLORIDE

A mixture of 100 g of m-anisic acid (0.658 mole), 250 g thionyl chloride (2.10 mole), and 5 ml dimethylformamide was heated under reflux in a round-bottom flask with desiccant in the top of the condenser for exclusion of atmospheric moisture. Excess thionyl chloride was distilled from the product using a rotary film-evaporator at about 200 torr (26.6 kPa). The m-anisoyl chloride was then isolated by fractional distillation through a 25 cm Vigreux column at 109° C./12 torr (1.6 kPa). Yield was 90 g (0.528 mole), i.e., about 80%.

PREPARATION OF 3,4'-DIMETHOXYBENZOPHENONE

A round-bottom flask was fitted with a stirrer, dropping funnel, nitrogen inlet, and thermometer. It was cooled in an ice/water bath. The initial charge was a mixture of 69.0 g anisole (0.638 mole), 90 g anhydrous aluminum trichloride (0.675 mole), and 108 g tetrachloroethane. It was cooled to below 15° C., with stirring, while a slow current of nitrogen was passed over the mixture. A solution of 90 g m-anisoyl chloride (0.528 mole) in 108 ml tetrachloroethane was added via the dropping funnel at a rate avoiding temperature increase of the stirred mixture to above 15° C. (addition period of 1 to 2 hr.). Following mixing, the flask stood two days at room temperature before ice (ca. 250 g) was carefully added to decompose the AlCl$_3$ complex. The tetrachloroethane was removed by steam distillation. The organic products were separated from the aqueous mixture by extracting into 500 ml of methylene chloride followed by drawing off and discarding the aqueous layer. Two washes of the methylene chloride solution with about 200 ml of 5% aqueous sodium hydroxide, and one wash with about 200 ml of water followed, removing and discarding the aqueous layer each time. After distilling off the methylene chloride using a rotary film-evaporator, 102 g of 3,4'-dimethoxybenzophenone (0.42 mole) remained which crystallized on cooling to room temperature. It was recrystallized from ethanol to yield 87 g (0.36 mole) of crystals melting at 53°–55° C. This material is also described along with its preparation in J. Am. Chem. Soc. 54 (1932) p. 1449.

PREPARATION OF 3,4'-DIHYDROXYBENZOPHENONE

Demethylation was accomplished by heating under reflux, for 15 hr., a mixture of 87 g 3,4'-dimethoxybenzophenone (0.36 mole) and a previously prepared mixture of 240 ml of 48% aqueous hydrobromic acid, 120 ml acetic anhydride, and 120 ml acetic acid. The dihydroxy product was isolated by pouring the cooled reaction mixture into about 400 ml water, filtering, washing with water, and drying in an oven at 80° C. Melting point was 193°–194° C. Yield was 77 g (0.36 mole), i.e., about 100%.

PREPARATION OF 3,4'-DIACETOXYBENZOPHENONE

To a slurry, in a beaker, of 73 g 3,4'-dihydroxybenzophenone (0.34 mole) in 225 ml acetic anhydride were added 8 drops of concentrated sulfuric acid, and the mixture was heated 30 min. on a steam bath. The resultant clear solution was cooled and then poured into about 600 ml water to precipitate the product. It was filtered, washed with water, and dried in an oven at about 80° C. Recrystallization from methanol yielded 80 g of diacetoxybenzophenone (0.268 mole) melting at 81°–83° C.

EXAMPLE II—Polyterephthalate of 3,4'-dihydroxybenzophenone

The polymerization apparatus was a 250 ml 3 necked flask equipped with: (1) a glass stirrer mounted in a pressure-tight resin bushing, (2) a nitrogen inlet, (3) a short Vigreux column leading to a water-cooled condenser with a flask for collecting acetic acid, and (4) an electrically heated Woods metal bath mounted for vertical height adjustment. Provision for application of a vacuum was in the distillation adapter.

The flask was charged with 9.57 g of diacetoxybenzophenone (0.032 mole) and 4.98 g of terephthalic acid (0.03 mole) and heated, with stirring, under nitrogen at atmospheric pressure from 238° C. to 310° C. in 48 min. Most of the acetic acid by-product was liberated in this time. Heating at 310° C. continued 22 min. more. Then a vacuum of 0.2 torr (0.0266 kPa) was applied, and a temperature was raised to 325° C. in 8 min. and maintained for 17 min. The cooled polymer had an inherent viscosity, $\eta_{inh}$, of 0.78. Its melt was anisotropic above its flow temperature of 296° C. using the TOT test.

The comminuted solid polymer was molded into a cylindrical plug and spun using a press-spinner through a 0.009 inch (0.23 mm) diameter spinneret hole at 325° C. under pressure of 700 psi (4830 kPa). Wind-up speed was 1000 ypm (914 m/min). Averaged filament properties were:

D/T/E/Mi=3.54/5.03/1.77/360
(3.92/4.45/1.77/318).

The filament was loosely wound on a soft bobbin and heated in an oven in slowly flowing nitrogen as follows: 220° C./1 hr.+240° C./1 hr.+260° C./1 hr.+280° C./1 hr.+300° C./1 hr. After this heating, averaged filament tensile properties were (denier substantially unchanged):

T/E/Mi=11.63/3.76/362 (10.28/3.76/320).

The best single values of tensile properties after heating were:

T/E/Mi=19.98/6.02/426 (17.66/6.02/376.5).

EXAMPLE III—Poly-2,6-naphthalenedicarboxylate of 3,4'-dihydroxybenzophenone

The procedure of Example II was used to polymerize 9.84 g of 3,4'-diacetoxybenzophenone (0.033 mole) with 6.48 g of 2,6-naphthalenedicarboxylic acid (0.030 mole). Polymerization temperature at atmospheric pressure increased from 235° C. to 345° C. in 87 minutes, and under vacuum from 345° C. to 365° C. in 40 minutes. Inherent viscosity, $\eta_{inh}$, was 0.78. In the TOT test, the melt was anisotropic above the flow temperature of 298° C.

A plug from the comminuted solid product was molded and spun as in Example II except that extrusion temperature was 360° C. and extrusion pressure was 400 psi (2760 kPa). Averaged filament properties were:

D/T/E/Mi=9.11/4.73/1.37/383
(10.12/4.18/1.37/338).

Heating under nitrogen, as in Example II, at 225° C./24 hr.+300° C./19 hr. improved average tensile properties to:

T/E/Mi=15.88/4.67/349 (14.04/4.67/308).

EXAMPLE IV—Copoly-2,6-naphthalenedicarboxylate from 3,4'-dihydroxybenzophenone (90 mol %) and hydroquinone (10 mol %)

Following the procedure of Example II, copolyester was prepared from 14.35 g 3,4'-diacetoxybenzophenone (0.048 mole), 1.04 g 1,4-diacetoxybenzene (0.0054 mole), and 10.80 g 2,6-naphthalenedicarboxylic acid (0.050 mole). Polymerization temperature at atmospheric pressure increased from 310° C. to 352° C. in 50 min. and under vacuum maintained at 352° C. for 34 min. The comminuted solid polymer was thoroughly washed with acetone to extract materials of low molecular weight. Inherent viscosity, $\eta_{inh}$, was 0.59. In the TOT test, the melt was anisotropic above the flow temperature of 323° C.

A molded plug of the copolyester was spun as in Example II. The filament, wound at 600 ypm (549 m/min), had averaged properties:

D/T/E/Mi=4.30/4.87/1.67/316
(4.78/4.30/1.67/279).

It was heated as described in Example II at 225° C./24 hr.+280° C./21 Hr.+300° C./16 hr. to yield tensile properties:

T/E/Mi=14.03/4.90/344 (12.40/4.90/304).

EXAMPLE V—Copolyester of 3,4'-dihydroxybenzophenone with 2,6-naphthalenedicarboxylic acid (90 mol %) and isophthalic acid (10 mol %)

A mixture of 15.95 g 3,4'-diacetoxybenzophenone (0.0535 mole), 0.83 g isophthalic acid (0.005 mole), and 9.7 g 2,6-naphthalenedicarboxylic acid (0.045 mole) was polymerized as described in Example II. Polymerization temperature at atmospheric pressure increased from 305° C. to 358° C. in 53 min. and under vacuum maintained at 358° C. for 17 min. Inherent viscosity, $\eta_{inh}$, was 0.92, and the TOT test showed melt anisotropy above the flow temperature of 303° C.

A plug molded from the comminuted solid copolyester was spun to a filament as described in Example II. The plug was at 380° C., the spinneret at 385° C., the spinning pressure was 600 psi (4140 kPa), and the windup speed was 600 yd/min. (549 m/min). The as-spun filament had averaged properties:

D/T/E/Mi=5.64/4.78/2.63/283
(6.26/4.22/2.63/250).

After heating as in Example II at 200° C./24 hr.+225° C./3 hr.+250° C./20 hr., the averaged tensile properties were:

T/E/Mi=8.34/4.14/269 (7.37/4.14/238).

EXAMPLE VI—Preparation of 3,4'-dimethoxy-4-methylbenzophenone

The procedures and equipment used in this monomer preparation are as described in Example I. A solution of 94.5 g m-anisoyl chloride (0.554 mole) in 113 ml of tetrachloroethane was added dropwise to a stirred, cooled mixture of 80.7 g o-methylanisole (0.661 mole), 94.5 g anhydrous aluminum chloride, and 113 ml tetrachloroethane, keeping the temperature of about 15° C. The mixture stood at room temperature for 24 hr. After adding ice and extracting with methylene chloride as in the preparation of 3,4'-methoxybenzophenone of Example I, an impure liquid was obtained from which the 3,4'-dimethoxy-4-methylbenzophenone was obtained by fractional distillation in a 25 cm Vigreux column at 198° C. and 2.0 torr (0.27 kPa) pressure. Yield was 114 g (0.445 mole).

Preparation of 3,4'-dihydroxy-4-methylbenzophenone

Demethylation of 114 g 3,4'-dimethoxy-4-methylbenzophenone (0.445 mole) was effected by refluxing 15 hr. with a previously prepared mixture of 313.5 ml of 48% aqueous hydrobromic acid, 148 ml of acetic anhydride, and 148 ml of acetic acid. The isolated product melted at 173°–174° C. Recrystallization from ethanol/water yielded 79 g (0.346 mole) of 3,4'-dihydroxy-4-methylbenzophenone melting at 174°–175° C.

Preparation of 3,4'-diacetoxy-4-methylbenzophenone

The 79 g of 3,4'-dihydroxy-4-methyl-benzophenone (0.346 mole) was acetylated using 237 ml of acetic anhydride and 8 drops of concentrated sulfuric acid and heating for 30 min. on a steam bath. The product was precipitated in water, filtered, washed and dried at about 80° C. After crystallizing the product from methanol, melting point was 60°–64° C. Yield was 87 g (0.279 mole). Before polymerization, this product as once more crystallized from methanol.

Polyester from bibenzoic acid and 3,4'-diacetoxy-4-methylbenzophenone

Polymerization of 10.89 g bibenzoic acid (0.045 mole) and 14.36 g 3,4'-diacetoxy-4-methylbenzophenone (0.046 mole) used the equipment and procedure of Example II. Heating at atmospheric pressure from 290° C. to 357° C. occurred in 80 min., and heating under vacuum at 357° C. was for 19 min. Inherent viscosity, $\eta_{inh}$, of the product was 1.09. The TOT test showed anisotropy of the melt above the flow temperature of 311° C.

A cylindrical molded plug of the comminuted product was spun as described in Example II with the plug at 378° C. and under 200 psi (1380 kPa) pressure. Windup speed was 400 yd/min. (366 m/min.). Averaged as-spun filament properties were:

D/T/E/Mi=8.0/4.15/1.15/382 (8.9/3.67/1.15/338).

After heating the filament as in Example II at 200° C./2 hr.+250° C./2 hr.+260° C./1 hr.+280° C./1 hr.+305° C./20 hr., the averaged tensile properties were:

T/E/Mi=8.31/2.90/303 (7.34/2.90/268).

EXAMPLE VII—Synthesis of 3-hydroxy-4'-(4-hydroxyphenyl-)benzophenone

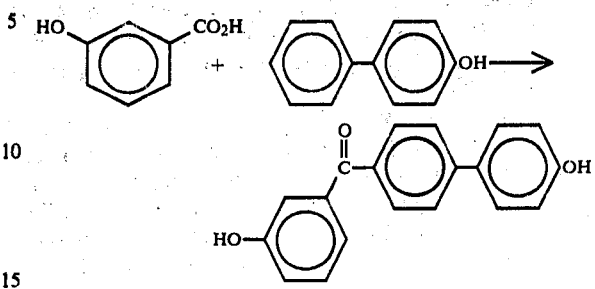

A 1 l. autoclave was charged with 85.0 g 4-phenylphenol (0.5 mole), 69.0 g 3-hydroxybenzoic acid (0.5 mole) and 500 ml HF (cooled to 0° C.). The autoclave was closed, air removed by flushing with $BF_3$. While maintaining the autoclave at 0° C. for 6 hr with shaking, $BF_3$ was applied to the contents at a pressure of 30 psi, (207 kPa).

At the end of this time the reaction mixture was poured into an excess of water (about 2 l.) to precipitate the crude product. This was filtered off, washed well with water and dried.

Yield of crude product, 136 g (94%)

M.p. of crude product, 213°–9° C.

The above crude product was heated under reflux for 2 hr with about 400 ml acetic anhydride and 0.15 g sulfuric acid. The product was isolated by precipitation of the $Ac_2O$ solution into about 2 l. water. Filtered, washed and dried.

Yield of crude product, 183 g (theory 187)

M.p. of crude product, 95°–9° C.

It was recrystallized from ethanol, m.p. 119°–121° C.

EXAMPLE VIII—Polyterephthalate of 3-hydroxy-4'-(4-hydroxyphenyl-)benzophenone The polymerization apparatus was similar to that used in Example II. The flask was charged with 15.56 g of the diacetate of 3-hydroxy-4'-(4-hydroxyphenyl-)benzophenone (0.042 mole, 4% excess) and 6.64 g terephthalic acid (0.040 mole) and heated with stirring, under nitrogen at atmospheric pressure from 280° C. to 346° C. in 35 min. Then a high vacuum was applied and heating was continued at 346° C. for 7 min. The cooled polymer had an inherent viscosity, $\eta_{inh}$, of 0.76 (measured in 7.5% trifluoroacetic acid, 17.5% methylene chloride, 12.5% dichlorotetrafluoro acetone hydrate, 12.5% Perclene ® and 50% 4-chlorophenol).

The polymer was spun as in Example II at 300° C. and the filament wound at 549 m/min. The resulting filament had an average denier of 8.6 dtex and average tensile properties T/E/Mi=2.21/0.76/448. After heating strengthening as described in Example II at 230° C./2 hr.+250° C./2 hr+270° C./1 hr+280° C./18 hr, the following average tensile properties were obtained:

T/E/Mi=5.85/2.95/226

EXAMPLE IX—Polyester from 3-hydroxy-4'-(4-hydroxyphenyl-)benzophenone and 2,6-naphthalenedicarboxylic acid The polymerization was similar to that of Example VIII except that 8.64 g of 2,6-naphthalenedicarboxylic acid (0.040 mole) was used in place of terephthalic acid. The initial heating from 268° C. to 340° C. was for 31 min under nitrogen at atmospheric pressure. The heating under vacuum was for 2 min at 340° C. to 344° C. The polymer had an inherent viscosity, ηinh of 0.73 as determined using the solvent employed for this purpose in Example VIII.

The polymer was melt spun as in Example II at 276° C. and the filament was wound up at 366 m/min. The melt spun filaments had an average denier of 7.6 dtex and average tensile properties T/E/Mi=1.41/0.54/234. After heat strenghtening as described in Example II at 220° C./2 hr+240° C./2 hr+260° C./2 hr+280° C./2 hr+304° C./18 hr, the following average tensile properties were obtained:

T/E/Mi=4.79/2.3/231.

I claim:

1. A fiber-forming (co)polyester consisting essentially of units having the structural formulas—

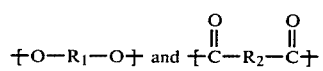

wherein R₁ in at least 85 mol % of the

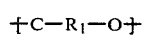

units is

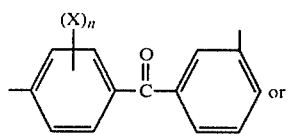

or

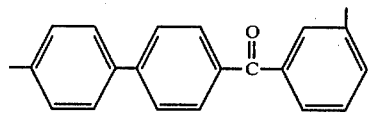

in which X is methyl or chloro and n is 0, 1 or 2 and wherein r₂ in at least 85 mol % of the

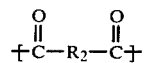

units is selected from the group consisting of p-phenylene, 2,6-naphthylene and p,p'-biphenylene with the proviso that when n is 1 or 2, R₂ is 2,6-naphthylene or p,p'-bi-phenylene.

2. The (co)polyester of claim 1 wherein R₁ in up to 15 mol % of the

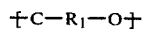

units is selected from the group consisting of m-phenylene, p-phenylene, chloro-p-phenylene, methyl-p-phenylene, p,p'-biphenylene, tetramethyl-p,p'-biphenylene, 2,6-naphthylene and 2,7-naphthylene and wherein R₂ in up to 15 mol % of the

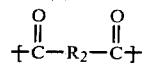

units is m-phenylene.

3. The (co)polyester of claim 1 wherein R₁ is

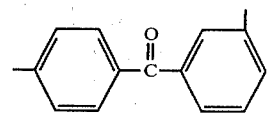

4. The (co)polyester of claim 3 wherein R₂ is p-phenylene.

5. The (co)polyester of claim 3 wherein R₂ is 2,6-naphthylene.

6. The (co)polyester of claim 1 wherein R₂ is 2,6-naphthylene.

7. The (co)polyester of claim 1 wherein R₂ is p,p'-biphenylene.

8. A filament of the (co)polyester of claim 1.

9. A heat-treated filament according to claim 8 and having a modulus of greater than 200 g/denier (177 dN/tex) and a tenacity in excess of 10 g/denier (8.84 dN/tex).

10. The (co)polyester of claim 1 wherein R₁ is

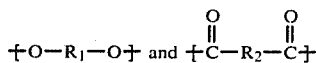

11. The (co)polyester of claim 10 wherein R₂ is p-phenylene.

12. A fiber-forming (co)polyester consisting essentially of units having the structural formulas

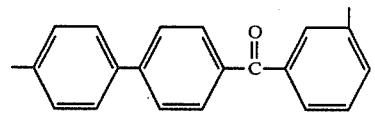

wherein R₁ is

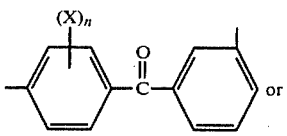

or

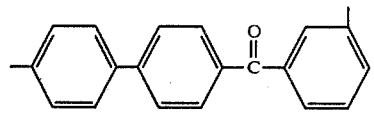

in which X is methyl or chloro and n is 0, 1 or 2 and wherein R₂ is selected from the group consisting of p-phenylene, 2,6-naphthylene and p,p'-biphenylene with the proviso that when n is 1 or 2, R₂ is 2,6-naphthylene or p,p'-biphenylene.

13. A fiber-forming (co)polyester consisting essentially of units having the structural formulas

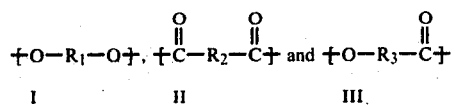
wherein $R_1$ is
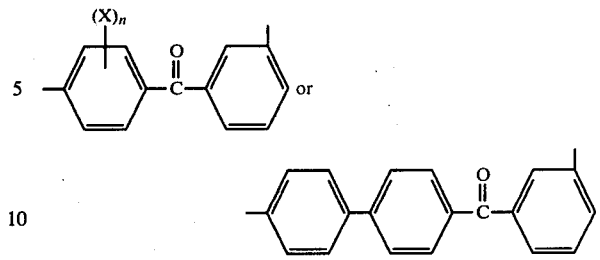
in which X is methyl or chloro and n is 0, 1 or 2, $R_2$ is p-phenylene, 2,6-naphthylene or p,p'-biphenylene and $R_3$ is m- or p-phenylene with unit III constituting up to 15 mol % of the total of units I and III.
14. A filament of the (co)polyester of claim 11.
15. A filament of the (co)polyester of claim 13.